United States Patent
Groth et al.

(10) Patent No.: US 6,951,219 B2
(45) Date of Patent: *Oct. 4, 2005

(54) TREATMENT OF HEPATITIS C USING HYPERTHERMIA

(75) Inventors: Karl Emil Groth, St. Paul, MN (US); Theodore Charles Kelly, Minnetonka, MN (US); Todd L. Westerbeck, Burnsville, MN (US); Gary Blick, Stamford, CT (US)

(73) Assignee: First Circle Medical, Inc., Minneapolis, MN (US)

( * ) Notice: Subject to any disclaimer, the term of this patent is extended or adjusted under 35 U.S.C. 154(b) by 20 days.

This patent is subject to a terminal disclaimer.

(21) Appl. No.: 10/667,917

(22) Filed: Sep. 22, 2003

(65) Prior Publication Data

US 2004/0055609 A1 Mar. 25, 2004

Related U.S. Application Data

(63) Continuation of application No. 09/951,830, filed on Sep. 13, 2001, now Pat. No. 6,644,320, which is a continuation of application No. 09/484,360, filed on Jan. 14, 2000, now Pat. No. 6,347,633.

(51) Int. Cl.$^7$ ............................................... A61B 19/00
(52) U.S. Cl. ...................................... 128/898; 604/6.13
(58) Field of Search ......................... 128/898; 604/6.13

(56) References Cited

U.S. PATENT DOCUMENTS

| 4,298,006 A | 11/1981 | Parks |
| 5,391,142 A | 2/1995 | Sites et al. |
| 5,486,208 A | 1/1996 | Ginsburg |
| 5,674,190 A | 10/1997 | Kelly |
| 5,730,720 A | 3/1998 | Sites et al. |
| 6,172,046 B1 | 1/2001 | Albrecht |
| 6,347,633 B1 | 2/2002 | Groth et al. |
| 6,644,320 B2 | 11/2003 | Groth et al. |

FOREIGN PATENT DOCUMENTS

| DE | WO 97/06839 | * 2/1997 | ............ A61M/1/36 |
| DE | 195 31 935 A1 | 2/1997 | |

OTHER PUBLICATIONS

Alonso et al., "Whole–Body Hyperthermia and the Augmentation of Cellular Cytotoxic Responses in the Treatment of Acquired Immune Deficiency Syndrome,"*Southern Medical Journal*, 88(10):S142 (1995).

Alonso et al., "Systemic Hyperthermia in the Treatment of HIV–related Disseminated Kaposi's Sarcoma,"*Am. J. Clin. Oncol. (CCT)*, 17(4):353–359 (1994).

Alonso et al., "Systemic Hyperthermia in the Treatment of HIV–related Disseminated Malignancy. Long–Term Follow–Up of Patients Treated with High Flow or Low Flow Extracorporeal Perfusion Hyperthermia," approximate date 1992 (18 pages).

Alonso et al., "Systemic Hyperthermia in the Treatment of HIV–related Kaposi's Sarcoma. A Phase I Study," *Biomed. & Pharmacother*, 46(1):21–24 (1992).

(Continued)

*Primary Examiner*—Thomas Barrett
(74) *Attorney, Agent, or Firm*—Popovich, Wiles & O'Connell, P.A.

(57) ABSTRACT

The invention provides a method of treating a patient infected with hepatitis C virus (HCV) comprising raising the core temperature of the patient and then returning the core temperature of the patient to normal at least one time, wherein the core temperature is raised to a temperature range and a duration sufficient to reduce or eliminate the patient's viral load of HCV.

56 Claims, 6 Drawing Sheets

OTHER PUBLICATIONS

"Backgrounder –Summary of Findings, Site Visit Report–Clinical Use of Hyperthermia in AIDS," National Institute of Allergy and Infectious Diseases, Sep. 4, 1990 (5 pages).

"Extracorporeal Whole Body Hyperthermia," First Circle Medical, Inc., Doc. No. 1600002, 1999 (71 pages).

Feb. 25, 1994 Letter from the Department of Health and Human Services forwarding the "Full Report of the Site Visit Report –Clinical Use of Hyperthermia in AIDS" (24 pages, including cover letter).

Internal Medicine Specialists "From Mercury to Malaria to Penicillin: The History of the Treatment of Syphilis at the Mayo Clinic, 1916–1955" reprint of Journal of the American Academy of Dermatology, 1995; 32:255–261.

Logan et al., "Case Report, Total Body Hyperthermia in the Treatment of Kaposi's Sarcoma in an HIV Positive Patient," *Med. Oncol. & Tumor Pharmacother*, 8(1):45–47 (1991).

More, "Hyperthermia Finds Little Effect," *GMHC Treatment Issues*, vol. 9, No. 11, Nov. 1995 (2 pages).

Pontiggia et al., "Whole Body Hyperthermia Associated with Betacarotene Supplementation in Patients with AIDS," *Biomed. & Pharmacother*, 5:263–265 (1995).

Pontiggia et al., "Whole–Body Hyperthermia Followed by Beta Carotene Supplementation in Patients with Acquired Immune Deficiency Syndrome (AIDS)," *Southern Medical Journal*, 88(10):S142 (1995).

PR Newswire "C. Everett Koop Joins First Circle Medical Board Former U.S. Surgen General Supports Company's Effort to Develop a New Treatment for Patients with AIDS and Other Diseases" p. 1, 1998.

Shecterie et al., "More on Hepatitis C", *The Scientist*, May 24, 1999.

* cited by examiner

TREATMENT OF HEPATITIS C USING HYPERTHERMIA

This application is a continuation of U.S. application Ser. No. 09/951,830, filed Sep. 13, 2001 now U.S. Pat. No. 6,644,320, which is a continuation of U.S. application Ser. No. 09/484,360, filed Jan. 14, 2000, now U.S. Pat. No. 6,347,633, issued Feb. 19, 2002, the contents of each of which are hereby incorporated herein by reference.

FIELD OF THE INVENTION

This invention relates to hyperthermic treatment of hepatitis C.

BACKGROUND OF THE INVENTION

Injected drug users are the largest group of people with hepatitis C infection. People who received a blood transfusion or kidney transplant before a diagnostic test became available form another large group of those infected.

Since human immunodeficiency virus (HIV) is also common among injected drug users and is transmitted sexually, about forty percent of HIV infected patients are co-infected with HCV. Various types of HIV such as HIV-1 and HIV-2 exist. Hepatitis C virus occurs in six known genotypes and more than fifty subtypes. The hepatitis C virus is harbored in the liver and most people infected with HCV eventually will develop cirrhosis or liver carcinoma. HCV can cause an acute or chronic infection. In chronic infection, the infected person can exhibit signs of chronic hepatitis or be a chronic asymptomatic carrier.

Current treatments for hepatitis C include interferons and other pharmaceuticals. However, because these treatments are not effective for all patients, improved methods for treating hepatitis C are being sought.

SUMMARY OF THE INVENTION

The invention provides a method for treating a patient infected with hepatitis C virus (HCV) comprising raising the core temperature of the patient and then returning the core temperature of the patient to normal at least one time. The core temperature is raised to a temperature range, a duration, and a number of times sufficient to reduce or eliminate the patient's viral load of HCV. In another embodiment of the invention, the patient is co-infected with the human immunodeficiency virus (HIV).

The invention also provides a method for treating a patient infected with HCV comprising raising the temperature of the patient's liver and then returning the temperature of the patient's liver to normal at least one time. The temperature of the patient's liver is raised to a temperature range, a duration, and a number of times sufficient to reduce or eliminate the patient's viral load of HCV.

It is to be understood that both the foregoing general description and the following detailed description are exemplary and explanatory and are intended to provide further explanation of the invention as claimed.

DETAILED DESCRIPTION OF THE INVENTION

The invention provides a method for treating a patient infected with hepatitis C virus (HCV) comprising raising the core temperature of the patient and then returning the core temperature of the patient to normal at least one time. The core temperature is raised to a temperature range, a duration, and a number of times sufficient to reduce or eliminate the patient's viral load of HCV. "Treating" in this application means raising the core temperature to a temperature range, a duration, and a number to times sufficient to reduce of eliminate the patient's viral load of HCV.

"Returning the core temperature of the patient to normal" includes allowing the patient to cool through ambient heat loss and actively cooling the patient. In the examples described below, the patient is cooled by ambient heat loss and active cooling to a temperature of 39° C. The patient is released from the hospital and the patient's temperature gradually returns to normal (37° C.) over a period of a few days. In one embodiment, the core temperature of the patient is raised and returned to normal one time. In another embodiment, the core temperature of the patient is raised and returned to normal two or more times. In one embodiment, the core temperature is raised by circulating the patient's blood from the patient, through an extracorporeal blood flow circuit, and back to the patient, wherein the blood returned to the patient has been heated within the blood flow circuit to an elevated temperature range. The patient's blood can be circulated from the patient through a blood vessel and returned to the patient through a blood vessel. In one embodiment, the patient's blood is circulated from the patient through a vein and returned to the patient through a vein. In another embodiment, the patient's blood is circulated from the patient through an artery and returned to the patient through a vein. In another embodiment, the core temperature is raised by inserting a heating element into the patient and the heating element heats the patient's blood. The heating element can be inserted into a blood vessel of the patient.

The heating element can be inserted into a central vessel, i.e., aorta or vena cava, where it can heat the blood passing by and eventually heating the blood to such a degree that the net temperature gain exceeds the losses due to the normal (physiologic) cooling mechanisms. Over time the body temperature can be raised to a predetermined point and maintained for a predetermined time. The heating element can be housed within a sheath or catheter at one or multiple positions along its length. The sheath or catheter can contain wires, conduits, fiberoptic, or other materials to supply power to the heating element. External to the body there could be a plug to connect the sheath or catheter to the control system. The sheath or catheter can be treated to give it antithrombogenic properties. This treatment can be chemical or a high energy corona or plasma discharge in the presence of a monomeric gas. The method of insertion can be through a cut-down or percutaneously (Seldinger Technique).

The heating element's method of heating can be by an electrical heating, radiofrequency, or laser. The heating element should not exceed 50° C. at the surface that contacts blood.

Such a heating element can be used for core heating and can also be used for local or regional heating. For example, a percutaneous insertion into an artery with a hollow sheath or catheter can be made to accommodate a steering guidewire so the device can be placed into the hepatic artery. A second hollow catheter with a thermistor tip can be placed, via a venous percutaneous stick, into the hepatic vein for liver temperature.

Methods which heat the blood to raise the core temperature, such as extracorporeal whole body hyperthermia, are preferred. However, methods in which the core temperature is raised by other methods such as by infrared radiation, convection, or surface contact such as a heating blanket can also be used in the method of the invention.

The core temperature can be raised to a temperature range of from 38 to 48° C., more preferably 38 to 44° C., more preferably 41.8 to 42.2° C. The core temperature can be raised for a period of from 2 minutes to sixteen hours, a period of from one-half to three hours, a period of from one to two hours, a period of from 80 to 100 minutes, or for 90 minutes. The core temperature can be taken rectally. For purposes of this application, the "core temperature" means rectal temperature. Temperatures other than the rectal temperature can be taken in the practice of the invention, e.g., esphogeal, bladder, tympanic, or cardiac line temperatures. The relationship between such other temperatures and the rectal temperature is well known in the art and such measurement by other methods will allow determination of the core temperature as defined herein.

Recommended exposure times during extracorporeal whole body hyperthermia are given in Table 1 below.

TABLE 1

| Core Temperature (° C.) | Exposure (minutes) |
| --- | --- |
| 39 | 960 |
| 40 | 480 |
| 41 | 240 |
| 42 | 120 |
| 43 | 60 |
| 44 | 30 |
| 45 | 15 |
| 46 | 8 |
| 47 | 4 |
| 48 | 2 |

The patient's viral load of HCV can be determined at least once before the core temperature has been raised at least one time; at least once after the core temperature has been raised and returned to normal at least one time; at least two different times after the core temperature has been raised and returned to normal at least one time, or combinations thereof.

In embodiments of the invention, the patient's viral load of HCV is reduced by 30 percent or more one month after the core temperature has been raised and returned to normal at least one time, more preferably, by 50 percent or more, by 75 percent or more, by 90 percent or more, or by 95 percent or more. In a preferred embodiment, the patient's viral load of HCV is reduced to less than the sensitivity level of a branched DNA signal amplification test (an example of which is provided below) one month after the core temperature has been raised and returned to normal at least one time. This determination of the patient's viral load is made one month after the last of the hyperthermic treatments. In another preferred embodiment, the patient's viral load of HCV is reduced to less than the sensitivity level of a reverse transcriptase-polymerase chain reaction test (an example of which is provided below) one month after the core temperature has been raised and returned to normal at least one time.

In embodiments of the invention, the patient's viral load of HCV is reduced by 30 percent or more three months after the core temperature has been raised and returned to normal at least one time, more preferably, by 50 percent or more, by 75 percent or more, by 90 percent or more, or by 95 percent or more. In a preferred embodiment, the patient's viral load of HCV is reduced to less than the sensitivity level of such branched DNA signal amplification test three months after the core temperature has been raised and returned to normal at least one time. In another preferred embodiment, the patient's viral load of HCV is reduced to less than the sensitivity level of such reverse transcriptase-polymerase chain reaction test three months after the core temperature has been raised and returned to normal at least one time. This determination of the patient's viral load is made three months after the last of the hyperthermic treatments.

The method of the invention can further comprise treating the patient with a pharmaceutical indicated for hepatitis C. The efficacy of a pharmaceutical effective for treatment of HCV in some patients can be increased when combined with hyperthermia. The method of the invention can also comprise treating the patient with a pharmaceutical indicated for HCV where such pharmaceutical was not efficacious for stand alone treatment for HCV and when combined with hyperthermic treatment results in the pharmaceutical being efficacious in some patients. The patient can be treated with a single pharmaceutical effective against hepatitis C or with two or more pharmaceuticals effective against hepatitis C. The drug can be administered to the same patient at several points: before raising the core temperature of the patient at least one time, while the core temperature of the patient is raised, and after the core temperature of the patient has been raised and returned to normal at least one time, or combinations thereof.

The pharmaceutical can be selected from interferons, protease inhibitors, cytokines, or any combination of antiviral drugs. The pharmaceutical can be selected from ribavirin, lamivudine, interferon alfacon-1, interferon alfa-2a, interferon alfa-2b, interferon-alfa-n1, thymosin alpha-1, interleukin-2, interferon alpha-n3, ketoprofen, interferon beta-1a, interferon gamma-1b, interleukin-12, histamine dihydrochloride, thymalfasin, zidovudine, didanosine, zalcitabine, stavudine, abacavar, nevirapine, delaviridine, efavirenz, ritonavir, indinavir, nelfinavir, saquinavir, amprenavir, or combinations thereof. In a preferred embodiment, the pharmaceutical can be selected from an interferon, ribavirin, or lamivudine. In another preferred embodiment, the pharmaceutical is an alpha interferon. The pharmaceutical can also include antioxidants, non-steroidal anti-inflammatory drugs, and/or reactive oxygen free radical scavengers. Several pharmaceuticals are being studied and some are available for treatment of hepatitis C. Commercially available interferons include INFERGEN (interferon alfacon-1, manufactured by Amgen Inc., Thousand Oaks, Calif.), ROFERON-A, (interferon alfa-2a, manufactured by Roche Pharmaceuticals, Nutley, N.J.), INTRON A (interferon alfa-2b, manufactured by Schering Corporation, Kenilworth, N.J.), and WELLFERON (interferon alfa-n1, manufactured by Glaxo Wellcome Inc., Research Triangle Park, N.C.). Ribavirin (1-β-D-ribofuranosyl-1H-1,2,4-triazole-3-carboximide) in combination with INTRON-A is sold as REBETRON by Schering Corporation.

The patient infected with HCV might have an acute HCV infection or a chronic HCV infection. The patient might be co-infected with a pathogen. The pathogen might be a virus, a spirochete, or a bacterium. The virus might be a heat labile virus. The heat labile virus might be selected from herpesviruses, hepadnaviruses, togaviruses, flaviviruses, coronaviruses, rhabdoviruses, filoviruses, paramyxoviruses, othomyxoviruses, bunyaviruses, arenaviruses, or retroviruses. The heat labile virus might be HIV, hepatitis B virus, Ebstein-Barr virus, cytomegalovirus, or *varicella*-zoster virus. In a preferred embodiment, the heat labile virus is HIV. The spirochete might be from the genus *treponema, borrelia,* or *leptospira*. The spirochete might be *Treponema pallidum, Treponema pertenue, Treponema carateum, Treponema pallidum endemicum, Borrelia burgdorferi, Borrelia hermsii,* or *Leptospira interrogans*. The bacterium might be an aerobic or anaerobic bacterium.

The invention also provides a method for treating a patient infected with hepatitis C virus comprising raising the temperature of the patient's liver and then returning the temperature of the patient's liver to normal at least one time. The temperature of the patient's liver is raised to a temperature range, a duration, and a number of times sufficient to reduce or eliminate the patient's viral load of HCV. In embodiments of the invention, the temperature of the liver is raised by local, regional, or intraperitoneal hyperthermia. In addition, the liver can be heated by the methods for raising the core temperature that are described herein.

Conventional hyperthermia equipment can be used in the methods of the invention.

A number of different tests are used to determine if a person has been infected with hepatitis C. In many people, the first indication of a possible infection is an increase in the enzyme found in healthy liver cells called alanine aminotransferase (ALT) and aspartate aminotransferase (AST). If there are more of these enzymes in the blood than normal, it often means that liver damage is occurring.

Clinicians will also test specifically for the hepatitis C virus. One set of tests looks for the presence of antibodies to the hepatitis C virus. If the antibodies (also referred to as anti-HCV) are present in a person's blood, it usually means that the person has been infected with the hepatitis C virus.

Other tests that are frequently performed detect the presence of HCV RNA. The two tests that are used to measure HCV RNA are called the reverse transcriptase-polymerase chain reaction (RT-PCR) test and the branched chain DNA (bDNA) test. RT-PCR is a more sensitive test and can detect much lower amounts of the virus than the bDNA test. The bDNA test can detect large numbers of the virus in the blood, but cannot detect the virus if only a low amount of the virus is present. One bDNA test is the Chiron Quantiplex HCV-RNA 2.0 test, available from Chiron Diagnostics, Inc., Emeryville, Calif. One RT-PCR test is Amplicor HCV Monitor test, available from Roche Diagnostics, Molecular Systems Division, Nutley, N.J.

EXAMPLES

Two HIV/AIDS patients who were co-infected with hepatitis C and were failing or had failed HIV and HCV pharmaceutical therapies were treated. The patients received a single session of Extracorporeal Whole Body Hyperthermia (EWBH). The patients continued their HIV drug regimens until the hyperthermia treatment and discontinued their drug regimens for the treatment and follow-up period.

The two patients were failing pharmaceutical therapy, as defined by (A) an HIV PCR viral load $\geq 10,000$ on a stable antiviral regimen, and (B) the failure of two or more combination antiviral regimens composed of all three of the following categories: two nucleoside analogues, one non-nucleoside reverse transcriptase inhibitor and one protease inhibitor. The patients underwent a single hyperthermic treatment in which their core body temperature was raised to a maximum of $41.8 \pm 0.2°$ C. for 90 minutes.

The results of the EWBH treatments of the two patients are presented in Table 2.

TABLE 2

TREATED PATIENT DATA

| PATIENT ID | INTERVAL DATE (days) | HIV Viral Load | CD4 Lymphocytes | CD4 % | Bilirubin | Platelets | CK-MB Ratio | ALT | AST | HCV Viral Load |
|---|---|---|---|---|---|---|---|---|---|---|
| PATIENT 1 | | | | | | | | | | |
| Baseline | 0 | 60,961 | 108 | 20 | 1.0 | 94,000 | ND | 95 | 73 | 14.3 |
| Day 1 | 1 | 249,289 | 100 | 25 | 1.4 | 21,000 | 1.0 | 325 | 421 | ND |
| Days 3–7 | 3 | 100,641 | 72 | 30 | 1.1 | 43,000 | ND | 531 | 186 | 38.3 |
| Unscheduled | 24 | 69,021 | 102 | 12 | ND | 80,000 | ND | 100 | 64 | 8.38 |
| Month 1 | 33 | 37,813 | 112 | 13 | 0.9 | 147,000 | ND | 97 | 65 | 5.26 |
| Unscheduled | 45 | 70,632 | 133 | 14 | 0.9 | 109,000 | ND | 97 | 74 | 7.32 |
| Month 2 | 59 | 62,044 | 111 | 14 | 0.7 | 108,000 | ND | 88 | 75 | 1.36 |
| Unscheduled | 73 | 150,142 | 123 | 15 | 1.2 | 76,000 | ND | 78 | 57 | 0.65 |
| Unscheduled | 88 | 196,237 | 101 | 11 | 1.4 | 87,000 | ND | NA | NA | <0.20 |
| Unscheduled | 102 | 134,415 | NA | NA | NA | NA | ND | NA | NA | <0.20 |
| Month 4 | | | | | | | | | | |
| Month 6 | | | | | | | | | | |
| PATIENT 2 | | | | | | | | | | |
| Baseline | 0 | 157,599 | 7 | 2 | 0.4 | cancelled-hemolzed | NA | 60 | 82 | 1.1 |
| Day 1 | 1 | 410,332 | 4 | 3 | 0.7 | cancelled-hemolzed | NA | 214 | 439 | 11.7 |

TABLE 2-continued

TREATED PATIENT DATA

| PATIENT ID | INTERVAL DATE (days) | HIV Viral Load | CD4 Lymphocytes | CD4 % | Bilirubin | Platelets | CK-MB Ratio | ALT | AST | HCV Viral Load |
|---|---|---|---|---|---|---|---|---|---|---|
| Days 3–7 | 3 | 619,376 | 9 | 6 | 1.4 | 34,000 | NA | 125 | 199 | 14.0 |
| Month 1 | | | | | | | | | | |
| Month 2 | | | | | | | | | | |
| Month 4 | | | | | | | | | | |
| Month 6 | | | | | | | | | | |

NA = not available
ND = not done

The data in Table 2 show a dramatic decrease in the HCV viral load. The HCV viral load of Patient 1 decreased from 14.3 MEq/mL to less than 0.20 MEq/mL (the limit of the sensitivity of the test) in three months. The HCV viral load of the patients was determined with a Chiron Quantiplex HCV-RNA 2.0 test, which uses a branched DNA signal amplification method, and is available from Chiron Diagnostics, Inc., Emeryville, Calif. Both Patients 1 and 2 will be tested until six months from the date of the EWBH treatment or protocol failure. Patient 1 was on a regimen of lamivudine, indinavir, ritonavir, hydroxyurea, adetovir, and abacavir before the EWBH (this regimen was stopped during the trial) and used the following propylactic drugs during the trial: ibuprofen for lyme disease. Patient 2 was on a regimen of lamivudine and efavirenz before the EWBH (this regimen was stopped during the trial) and used the following propylactic drugs during the trial: VALTREX for herpes, PEPCID for reflux, alprazolam for anxiety, and BACTRIM for *Pneumocystis carinii* pneumonia. Table 2 also provides the HIV viral load (copies/mL), CD4 lymphocytes count (cells/mm$^3$), CD4%, bilirubin (mg/dL), platelets count (cells/mm$^3$), CK-MB ratio of intracellular enzymes, ALT (U/L), and AST (U/L).

According to the preferred embodiment, the two patients will be screened for subsequent hyperthermic treatment as follows. The patients will be followed until they experience a confirmed 0.5 log or greater increase in HIV viral load either (1) from baseline, if no decline in viral load is achieved after receiving EWBH, or (2) from the lowest recorded HIV viral load following EWBH. In the event a patient experiences a confirmed 0.5 log or greater increase in HIV viral load, they will be re-screened for eligibility of EWBH, and if eligible, will be offered another single session of EWBH and followed per protocol. The criteria for re-treatment will be a 0.5 log increase in HIV viral load above baseline or nadir, whichever is greater. The details of the clinical protocol followed for the two patients and the equipment used are presented below.

Clinical Protocal

The purpose of this investigation was to assess the efficacy of a single EWBH treatment in individuals who were failing pharmaceutical therapies for HIV. Failing pharmaceutical therapies is defined as (A) an increase in HIV PCR viral load to $\geq 10,000$ while on a stable antiviral regimen, and (B) the failure any two combination antiviral regimens composed of all three of the following categories: two nucleoside analogues, one non-nucleoside reverse transcriptase inhibitor and one protease inhibitor. A stable antiviral regimen is defined as no changes in antiretroviral regimen for sixteen weeks prior to screening for the study. Antiviral regimens will usually give peak PCR lowering within 8 to 16 weeks after initiation.

In the event a patient experiences a confirmed 0.5 log or greater increase in viral load from baseline or nadir, they will be re-screened for eligibility for EWBH, and if eligible, will be offered another single session of EWBH and followed per protocol. All patients will have blood work drawn and analyzed at screening, during treatment, and at follow-up as per protocol. The criteria for re-treatment will be a 0.5 log increase in viral load above baseline or nadir, whichever is greater.

Analysis of primary objective parameters included HIV viral loading as measured by Polymerase Chain Reaction (PCR), HIV-RNA, and CD4 cell counts and percentages. Secondary objective parameters included the assessment of the cumulative incidence of opportunistic infections in the EWBH treated verses the control populations. Clinical utility, data assessing quality of life, were followed to evaluate significance of this treatment, pre and post therapy.

Prophylactic medication was allowed during the protocol period and appropriate treatment was given for opportunistic infections. Prophylactic medication to minimize the risk for recurrent Herpes infection was allowed. Any HIV/AIDS physical lesions present prior to therapy was measured and, if possible, photographed so that these lesions can be followed post treatment.

Patients fulfilled the following criteria to be eligible and had no ineligibility exclusions:
1. Documentation of positive test for Human Immunodeficiency Virus (HIV-1) Enzyme Linked Immunosorbent Assay (ELISA), confirmed by Western Blot.
2. Were failing recommended pharmaceutical therapy as defined by (A) an HIV PCR viral load of $\geq 10,000$ while on a stable antiviral regimen (defined as no changes in antiretroviral regimen for sixteen weeks prior to screening for the study), (B) the failure of at least two combination antiviral regimens composed of 2 or more antiretroviral medications, and (C) prior use of at least two nucleoside analogues, one non-nucleoside reverse transcriptase inhibitor, and one protease inhibitor.
4. Karnofsky Performance status: $\geq 70\%$.
5. Male or female, age 18–60 years old, inclusive.
6. Granulocyte $\geq 500$/mm3; White Blood Count (WBC) $\geq 1500$/mm$^3$; platelet count $\geq 100,000$/mm$^3$; hematocrit $\geq 30$ vol %, and hemoglobin $\geq 10$ g/dl.
7. Prothrombin Time (PT), Activated Partial Thromboplastin Time (aPTT), antithrombin III, fibrinogen, and thrombin time $\leq 20\%$ of upper or lower limits of normal range.

8. Serum creatinine <2.0 mg/dL.
9. Serum aspartate aminotransferase (SGOT, AST) and Serum alanine aminotransferase (SGPT, ALT) ≦5×upper limit of normal.
10. Negative pregnancy test for females.
11. CD4+ lymphocyte helper cells ≦500 cells/mm$^3$.
12. Roche Amplicor HIV-1 RNA PCR ≧10,000 copies/ml.
13. Signed informed consent.
14. Stress Echocardiogram, or stress test and echocardiogram, or echocardiogram nucleotide studies with EF ≧45%, normal LV function and no evidence of coronary artery disease.
15. Forced Expiratory Volume (FEV1) ≧60% of expected function.
16. Negative CT scan of the brain with contrast.
17. Willingness to adhere to follow-up schedule.

Patients that exhibited any of the following were excluded from the protocol:
1. New York Heart Association (NYHA) classification III or IV.
2. History of a myocardial infarction, abnormal stress test suggesting ischemic changes, malignant, uncontrollable arrhythmia's or documented unstable angina within the last 12 months.
3. Major surgery within four weeks of protocol therapy.
4. History of central nervous system hemorrhage attributable to bleeding diathesis, or previously documented cerebrovascular accident.
5. Evidence of any active opportunistic infection. Patient must be at least four weeks status post therapy for opportunistic infection.
6. Allergic history to heparin, protamine, pork/beef products, fish, lidocaine or other anesthetic agents.
7. Uncontrolled hypertension, systolic BP 160 and diastolic BP 105.
8. Active illicit drug use determined by history.
9. Currently enrolled in other investigational clinical trial that would preclude participation in this protocol.

In the preferred embodiment, patients receiving EWBH treatment would continue their current drug regimens until EWBH treatment and then discontinue their drug regimens for the treatment and follow-up period. All EWBH-treated patients were be followed until they experienced a confirmed 0.5 log or greater increase in viral load either (1) from baseline, if no significant decline in viral load was achieved after receiving EWBH, or (2) from the lowest recorded viral load following EWBH. In the event an EWBH patient experienced a confirmed 0.5 log or greater increase in viral load from baseline or nadir, they were re-screened for eligibility of EWBH, and if eligible, were offered another single session of EWBH and followed per protocol. All patients were followed per protocol with serial collection of subjective and objective data. All data was be accumulated, tabulated and analyzed.

For purposes of analysis, all patients (EWBH and Control) remained on study until: (1) criteria for treatment is documented (≧0.5 log increase in PCR from baseline or nadir); (2) end of the six-month follow-up following initial randomization; or (3) loss to follow-up, withdrawal, or death during six-month follow-up.

Analysis of primary objective parameters included HIV viral load as measured by Roche Amplicor HIV-RNA PCR, available from Roche Diagnostics, Nutley, N.J., lymphocyte subset profile and percentages (CD4). Secondary objective parameters included the assessment of the cumulative incidence of opportunistic infections in the patients. Clinical utility, data assessing quality of life were followed to evaluate significance of this treatment, pre and post therapy. The observed risks (i.e., device-related and treatment related adverse events) of EWBH were monitored in relation to the potential benefits of the therapy.

Each patient was informed of all procedures to insure that there would be compliance with the visits required for treatment and for the follow-up process. Patients received the best available care for medical problems arising during the study. Current medications were noted at the time of screening and reported on the case report form. Drugs administered or taken during the trial were recorded on the case report form, specifying the type of medication, dose, schedule, duration and reason for its use. All hospital admissions, clinic/office visits, incidence of opportunistic infections, including treatment given and duration, were closely monitored and recorded on Serious Adverse Event (SAE) and Adverse Event (AE) forms.

Clinical history included the date of HIV/AIDS diagnosis, history of symptoms (dates and severity), and therapies previously administered, with duration of use and reasons for discontinuation. The history included all known allergies.

Clinical assessment included blood studies as listed in Table of Required Observations. Follow-up bloods were obtained at Day 1 post EWBH therapy and were repeated at follow-up clinic visits at day 3–7, months 1, 2, 4, and 6 months (±1 week) (to the extent that the patient had reached these time points).

The following studies were performed in addition to the physical examination. Pre-procedure blood sampling was obtained on the morning of admission. Additional tests were repeated throughout the study (see Table of Required Observations). Tests and procedures were repeated as necessary to assess clinical toxicity.

1. Hematology:
Complete Blood Count (CBC, including WBC) with differential
Blood type (ABO Rh)
2. Coagulation:
Prothrombin time (PT), Partial thromboplastin time (aPTT), Antithrombin III, Thrombin time, Fibrinogen
3. General chemistries:
Sodium, Potassium, Chloride, $CO_2$, Calcium, Phosphorous, Magnesium, Glucose, Albumin, Creatinine, Cholesterol, Total protein, ALT, AST, Total bilirubin, Alkaline phosphatase, Creatinine Phosphokinase (CPK), Lactate Dehydrogenase (LDH), Blood Urea Nitrogen (BUN),
4. Cardiac assessment:
Stress Echocardiogram with Electrocardiogram (EKG)
5. Pulmonary assessment:
Chest X-ray (CXR), Pulmonary Function Tests (1 Second Forced Expiratory Volume, FEV1, and Forced Vital Capacity, FVC)
6. Renal Function:
BUN, Creatine
7. Neurologic assessment:
Thorough neurological physical examination
Computed Axial Tomography (CAT) scan with contrast of the head 8. Immune system assessment:
Lymphocyte phenotype profile, including CD4, and CD8.
HIV RNA PCR (Roche Amplicor).
9. Chronic Hepatitis assessment:
Hep C Qual. PCR
Hep B Surface antigen
HepB DNA PCR (if HBSAg positive)
10. Measurement and documentation of any lesions, if appropriate by photographs.
11. Measure of overall Karnofsky performance status operating table was equipped with a foam rubber mattress and/or pads for flexor point protection.
2. Patient Instrumentation for EWBH:
   The following was placed in the operating room prior to EWBH:
   i. Swan-Ganz EKG lead monitoring
   ii. Peripheral intravenous (IV) lines (2),
   iii. Radial artery catheter
   iv. Pulmonary artery (Swan-Ganz type) thermistor catheter via central vein.
   v. Oximeter.

TABLE OF REQUIRED OBSERVATIONS

| Test/Procedure | SCREEN[1,2] | Days[1,2] | | | Months[1,2] | | | |
|---|---|---|---|---|---|---|---|---|
| | | 0 | 1 | 3 | 1 | 2 | 4 | 6 |
| Consent Form(s) | X | | | | | | | |
| ELISA/Western Blot | X | | | | | | | |
| HIV RNA PCR level | X | X | X | X | X | X | X | X |
| CD4/CD8 level | X | X | X | X | X | X | X | X |
| HepC Qual. PCR | X | | | | | X** | | X** |
| Hep C bDNA (Bayer) | X*** | X*** | X*** | X*** | X*** | X*** | X*** | X*** |
| HepBSAg | X | | | | | | | |
| HepB DNA PCR**** | X | X | X | X | X | X | X | X |
| HIV Genotype | | X | | X | | | | |
| History and Physical | X | X | X | X | X | X | X | X |
| CXR | X | | | | | | | |
| Hematology | X | X | X | X | X | X | X | X |
| Blood Type | X | | | | | | | |
| Coagulation | X | X | X | X | X | X | X | X |
| Biochemical Profile | X | X | X | X | X | X | X | X |
| Cardiac Assessment | X | | | | | | | |
| Pulmonary Assessment | X | | | | | | | |
| Urine Analysis & Culture | X | | | | | | | |
| Neurologic Assessment | X | | | | | | | |
| Karnofsky Status | X | X | | X | X | X | X | X |
| Lymph Node Biopsy[3] | | X | X | X | | | | X |
| Spinal Fluid Specimen[4] | | X | X | X | | | | X |
| Health Status Questionnaire | X | | | X | X | X | X | X |

*Any test, measurement, or assessment was performed at any time, as clinically indicated.
**If HCV Qualitative PCR is negative
***If HepC Qualitative PCR is positive
****If HBSAg is positive at screening
[1]EWBH treatment group
[2]Control group
[3]Lymph Node biopsies were performed on the patients 1 to 7 days prior to the EWBH treatment, at day 1, day 3–7, and Month 6 or prior to re-treatment with EWBH (to the extent the patient had reached these time points).
[4]Lumbar puncture was performed to obtain spinal fluid from the EWBH treated patients 1 to 7 days prior to the EWBH treatment, at day 1, day 3–7, and Month 6 or prior to re-treatment with EWBH (to the extent the patient had reached these time points).
Health Status Questionnaire was completed @ screening, Day 3, and months 1, 2, 4, 6.

The following protocol design was used in the hyperthermic treatment arm.
A. Pre Procedure:
   After the history, physical examination, and laboratory procedures had been completed, and entry criteria satisfied, the patient was admitted to the hospital on the day of the procedure. Bloods were drawn according to the Table of Required Observations. Patient was Nothing Per Os (NPO) for at least 6 hours prior to the procedure. Preoperative antibiotics were given prophylactically for 24 hours.
B. Procedural Parameters:
   Once in the Operating Room (OR) or treatment room s/he was placed upon the OR table and prepared for the procedure.
   1. Description of Treatment Facility:
      The OR or treatment room used for the procedure DID not have to be modified for this procedure. The vi. Urinary bladder catheter with thermistor.
   vii. Rectal temperature probe.
   viii Esophageal temperature probe (general anesthesia).
   ix Tympanic temperature.
   x. Bilateral femoral venous catheters was placed by a surgeon and connected to the hyperthermia unit
   Temperature probes (esophageal, rectal, and tympanic) were calibrated, within 0.1° C., to a NIST traceable device.
3. Anesthesia:
   Anesthetic management was the responsibility of the anesthesiologist administered appropriate agents according to the standard of care. The choice of anesthetic agent was determined based on individual patient profile. Either general anesthesia or sedative agents can be used.
   To ensure an adequate hourly urine volume, a dopamine drip at 2–3 mcg/kg/min was used throughout the procedure and in the early postoperative period. Average urinary flow of 30 cc/hr minimum was targeted. Fluid replacement during the procedure was administered at the discretion of the operating team. Albumin and mannitol were not used during the hyperthermia treatment.

4. EWBH conduct, all parameters were entered on case report forms:
   From the Swan Ganz catheter, serial readings of pulmonary systolic and diastolic pressures and blood temperature were recorded. Cardiac output (CO) as measured via the thermodilution catheter was measured prior to and following the treatment.

Each patient was continuously monitored at 5 minute intervals for temperature during the procedure. The perfusionist recorded all perfusion data on specific perfusion data forms. Other patient parameters were recorded on standard OR flow sheets.

Temperatures Monitored:
   Rectal ($T_R$), Esophageal($T_E$), Tympanic ($T_P$), Pulmonary Artery ($T_{PA}$), Water Inlet/Heat Exchanger ($T_W$), Blood Outlet/Heat Exchanger ($T_{Bld}$)

a. Preparation:
   The perfusionist primed the circuit with an isotonic solution, and circulated until totally de-aired. The surgeon cannulated the femoral veins using open or percutaneous methods for connection with the extracorporeal circuit.
   A predetermined dose of heparin required for extracorporeal circulatory bypass was calculated at 150 units/kg and administered in two 75 unit/kg doses with an Activated Clotting Time (ACT) determination before and after each dose. An ACT 2½ to 3 times normal was maintained during EWBH. Further doses of heparin, if needed, were administered according to ACT measurement.

b. Heating Phase:
   The time to reach a core temperature of 41.8°±0.2 was about 40 minutes.
   i. EWBH was initiated at a blood flow rate of approximately <20% of the baseline cardiac output. The water circulating through the heat exchanger did not exceed 50° C. for longer than 5 minutes.
   ii. When either $T_E$ or $T_R$ (whichever is greater) reached 41.8°±0.2° C., the plateau phase was begun.
   iii. When 40.0° C. is reached, ice packs were placed under and/or around the patient's neck.

c. Plateau Phase:
   i. Core body temperature ($T_E$, or $T_R$, whichever is greater) was maintained between 41.6–42.0° C. for 90 minutes. $T_W$ was reduced so that neither $T_E$ or $T_R$ exceeded 42.0° C. Since body temperature cannot be instantaneously changed, momentary excursions above 42.0° C. were not be considered protocol deviations.
   ii. Blood flow was altered to regulate blood and core temperature.

d. Cooling Phase:
   Anticipated time to reach 39° C. is 30–45 minutes.
   i. Cooling was initiated at first by discontinuing the water flow for the first 20 minutes, cooling by ambient heat loss.
   ii. After 20 minutes the thermostat was reset to 30° C., and the water flow re-instituted.
   iii. When $T_R$ reached 39° C., bypass was discontinued.
   iv. Decannulated and reversed heparin with protamine sulfate.

e. Once stable, the patient was transferred to the post anesthesia or recovery room.

| | | REQUIRED OBSERVATIONS DURING EWBH BY PHASE | | | | | | | | | | | | | |
|---|---|---|---|---|---|---|---|---|---|---|---|---|---|---|---|
| | | Warming | | | | Plateau | | | | | | | Cooling | | |
| Test* | Pre/ | 0 | 15 | 30 | 45 | 0 | 15 | 30 | 45 | 60 | 75 | 90 | 15 | 30 | |
| Post Blood gases | | X | X | X | X | X | X | X | X | X | X | X | X | X | X |
| Electrolytes | X | | | X | | | | X | | | | X | | | X |
| Biochemistry | X | | | | | | | | | | | | | | X |
| Hematology | X | | | | | | | | | | | | | | | X |
| Urine Analysis & Culture | X | | | | | | | | | | | | | | |
| CD4/CD8 | X | | | | | | | | | | | | | | |
| HIV RNA PCR | X | | | | | | | | | | | | | | |
| Hep C bDNA (Bayer)** | X | | | | | | | | | | | | | | |
| Hep B DNA PCR*** | X | | | | | | | | | | | | | | |
| HIV-1 Genotype | X | | | | | | | | | | | | | | |
| Coagulation | X | | | | | | | | | | | | | | | X |
| ACT only | X | X | X | X | X | X | X | X | X | X | X | X | X | X | X |
| Cardiac output | | X----------------------------------------------------------------X |
| Urine output | X----------------------------------------------------------------X |
| Pressure | | | | | | | | | | | | | | | |
|   Arterial | X----------------------------------------------------------------X |
|   Pulmonary | X----------------------------------------------------------------X |
| EKG | X----------------------------------------------------------------X |
| Temperature | X----------------------------------------------------------------X |
| CXR | | | | | | | | | | | | | | | X |
| Lymph Node Bx[1] | X | | | | | | | | | | | | | | |
| Lumbar Puncture[2] | X | | | | | | | | | | | | | | |

Legend: X = Discreet sample/monitor point
X----X = Continuous monitoring recorded at 15 ± 5 minute intervals
*Tests may be performed at any time following intervention.
**If Hep C Qual. PCR is positive at screening
***If Hep B DNA PCR is positive at screening
[1]Lymph node biopsy was performed on the patients 1 to 7 days prior to the EWBH treatment
[2]Lumbar puncture for spinal fluid analysis was performed in the patients prior to the EWBH procedure (1 to 7 days prior to the EWBH treatment)

C. Post-EWBH Patient Monitoring:
1. In the Post Anesthesia or Recovery Room, standard monitoring included:
   Continuous EKG monitoring
   12 lead EKG strip if indicated
   Temperature, pulse, respirations and blood pressures (every 15 minutes for the first one and one-half hours, then every half hour for the next one and one-half hours),
   Urinary output
2. At the time of discharge from the hospital, a CXR was obtained to rule out the presence of pulmonary problems such as pneumothorax, atelectasis, etc. Pressure dressing was removed from the femoral cannulation sites to confirm hemostasis.
3. Patients were discharged from the hospital when able to ambulate approximately 23 hours after admission.

Follow-Up Visits

Follow-up visits were required at day 1 between day 3–7, and 1 month (±7 days), 2 months (±7 days), 4 months (±7 days), and 6 months (±7 days) after the EWBH treatment (to the extent the patient had reached these time points). At follow-up visits the patient was questioned about possible adverse reactions since their last visit, and any reaction described was recorded on the case report form. Blood was drawn for clinical laboratory tests according to the Table of Required Observations.

Equipment Used

The contents of the following U.S. patents and patent applications are hereby incorporated by reference into this application: (1) U.S. Pat. No. 5,391,142, issued Feb. 21, 1995, and entitled "Apparatus and Method for the Extracorporeal Treatment of the Blood of a Patient Having a Medical Condition," (2) U.S. Pat. No. 5,674,190, issued Oct. 7, 1997, and entitled "Extracorporeal Whole Body Hyperthermia Using Alpha-Stat Regulation of Blood pH and $pCO_2$," (3) U.S. patent application Ser. No. 09/334,224, filed Jun. 16, 1999, entitled "Bladder Catheter for Hyperthermia System," and (4) U.S. patent application Ser. No. 09/334,520, filed Jun. 16, 1999, entitled "Thermal Sensor for Hyperthermia System".

The hyperthermia equipment used was composed of three main components: (a) the console, (b) a heater/cooler unit and (c) the disposable blood contact circuit.

The console was composed of an extracorporeal, centrifugal pump device used for the operating and monitoring of the hyperthermia procedure. It contained the drive motor and controllers for the pump and electronics for monitoring the system parameters (temperature, pressure, and flow). The heater/cooler unit was used to raise or lower the patient's temperature and maintain a desired patient temperature through conductive heat transfer. Heated water was circulated through the heat exchanger to elevate the patient's temperature. Cool water was circulated through the heat exchanger to reduce the patient's temperature.

The disposable blood contact circuit was comprised of components for inducing and monitoring hyperthermia. In order to complete the circuit, vascular access was required. Blood left the patient via a venous cannula and PVC tubing which directed it to a centrifugal pump. From the pump, the blood was propelled through the heat exchanger where thermal exchange occurred, with the assistance of the heater/cooler. After the blood was heated it passed through a blood filter before returning to the patient via a second venous cannula. Circuit temperature was monitored by a calibrated thermistor probe placed within the outlet of the heat exchanger. This represented the highest blood temperature reading in the circuit. The blood temperature and those temperatures recorded from the heater/cooler as well as patient temperatures were the basis of the perfusion management of blood flow and heater/cooler temperature during the procedure.

Circuit flow was measured by an electrically isolated electromagnetic flowmeter built into the console, and a flow insert that was located in the blood circuit. Flow rates values have been determined experimentally to be approximately <20% of the baseline cardiac output. At these flow levels the rate of temperature rise to the patient was gradual enough not to cause biochemical parameters to change drastically. Blood flow rate adjustment was used with water bath temperature adjustment to fine tune the process and maintain the core body temperature within a narrow range for the appropriate time.

Circuit pressure monitoring was accomplished by the pressure electronics built into the console and a disposable transducer which was located at the input side of the heat exchanger. This position within the circuit allowed the operator to monitor resistance to flow downstream of the pump. Changes in the pressure reading were used as a diagnostic tool to determine circuit integrity and the state of anticoagulation. A connection was made between the three-way stopcock, at the transducer, and the two-way stopcock at the pump input. With the three-way stopcock turned to isolate the pump inlet pressure, the operator was able to recognize a possible malposition of the egress cannula. By utilizing this reading in conjunction with the pulmonary artery diastolic pressure it was possible to anticipate changes in the patient's volume status. A 40 $\mu$m filter kept blood free of particulate matter.

The system was used to perform hyperthermia treatment of the patient's blood. The components and sub-assemblies were consolidated and coordinated to facilitate implementation of use. The apparatus included structures which defined an extracorporeal blood flow circuit. Such a circuit included a first cannula for use in cannulating a femoral vein of the patient. Such a cannula defined a blood egress point. A second cannula was used for cannulating a different femoral vein of the patient, and the second cannula defined a blood ingress point. A discontinuous conduit was provided to interconnect, in part, the first and second cannulae. A conduit portion of an integrated, sterile module had interposed therein a pump, a heat exchanger for regulating the temperature of blood flowing through the conduit portion, and sensors for ascertaining the temperature, pressure, and flow rate of blood passing through the conduit portion. The apparatus, further, employed a controller for regulating the pump and temperature regulators in response to temperature, pressure, and blood flow rates sensed by the sensors.

A console was employed with the module having various controls. Such controls were used for selectively changing settings to achieve desired pressure and blood flow rate through the conduit portion.

The integrated, sterile module was a disposable component. As a result, the medical treatment facility inhibited the possibility of contamination of the blood of one patient by HIV positive blood of a patient previously treated, and of health care workers involved in the treatment.

In cannulating a patient for extracorporeal blood circulation, a blood flow circuit was defined between a first point of cannulation at a vein of the patient and a second point of cannulation at a vein of the patient. The patient's blood was then pumped through the circuit As the blood passed through the circuit, it was heated to a first elevated temperature for a relatively short period of time. Thereafter, it was heated to a second elevated temperature, lower than the first elevated temperature, for a more extended period of time.

In an embodiment of the invention, the blood is heated to a first elevated temperature of between 42° C. to 48° C. The blood could, typically, be maintained at the first elevated temperature for a period of time of about one half to one hour. Thereafter, the blood could be maintained at the second elevated temperature for a period of about one to two hours. The second elevated temperature, it is envisioned, could be between 42 to 44° C. or 37° C. to 39° C.

Figure 2:
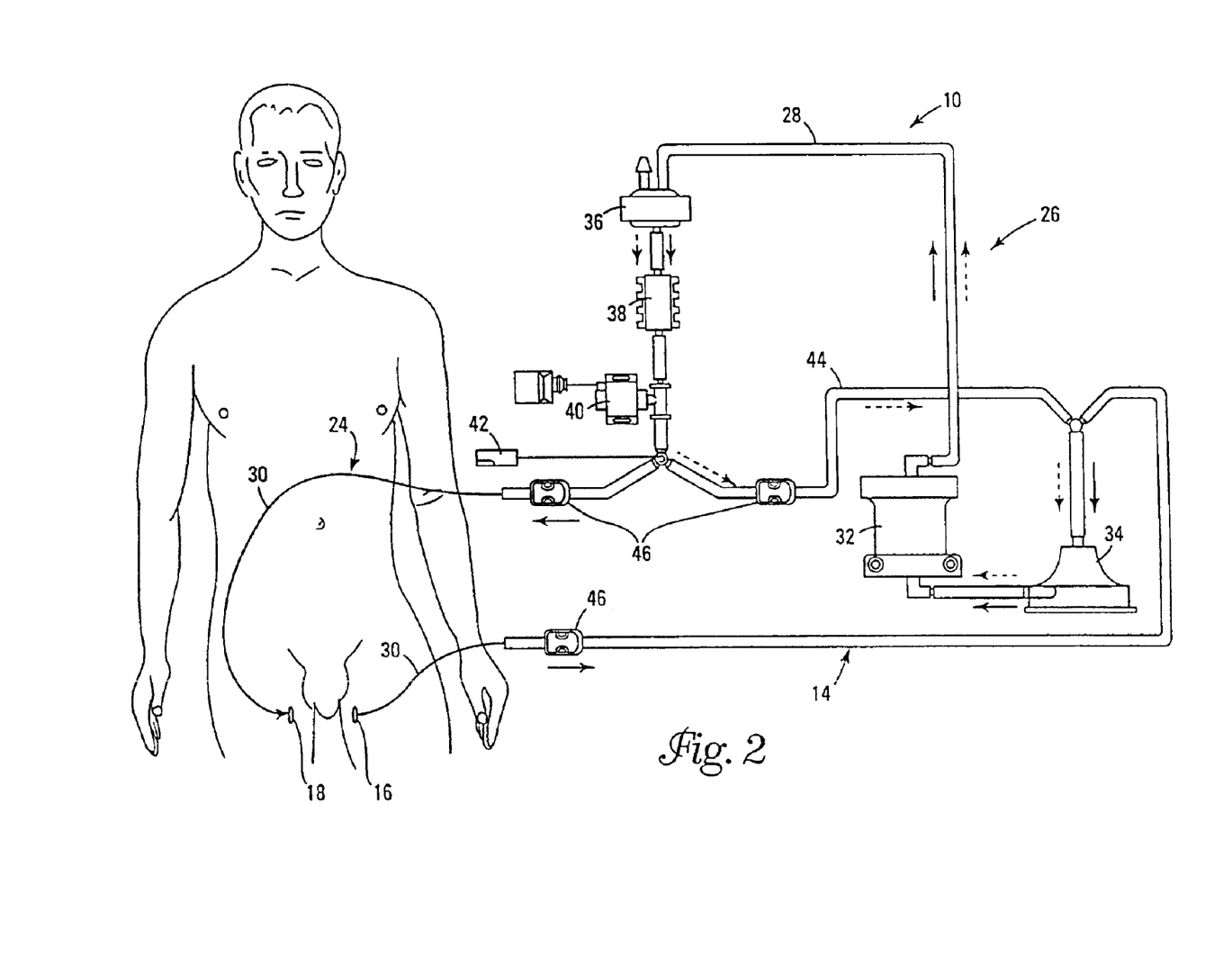
FIG. 2 is a mechanical diagram showing cannulation sites on a human adult.

Referring now to the drawings wherein like reference numerals denote like elements through the several views, FIG. 2 shows diagrammatically the apparatus 10 used in the hyperthermia treatment of the patients as a procedure for addressing hepatitis C infection. In FIG. 2, a femoral vein in the left leg was cannulated as a point of egress of blood from the patient's body (as at 16), and a femoral vein in the patient's right leg was cannulated as a point of ingress of the blood back into the patient (as at 18). It will be understood that these two specific points of cannulation 16, 18 are not exclusive and that other cannulation locations are specifically contemplated. The locations illustrated in FIG. 2, however, have been found to be particularly appropriate, and ingress and egress points in different legs have been shown as being utilized so that a single leg of the patient is not compromised.

Figure 1:
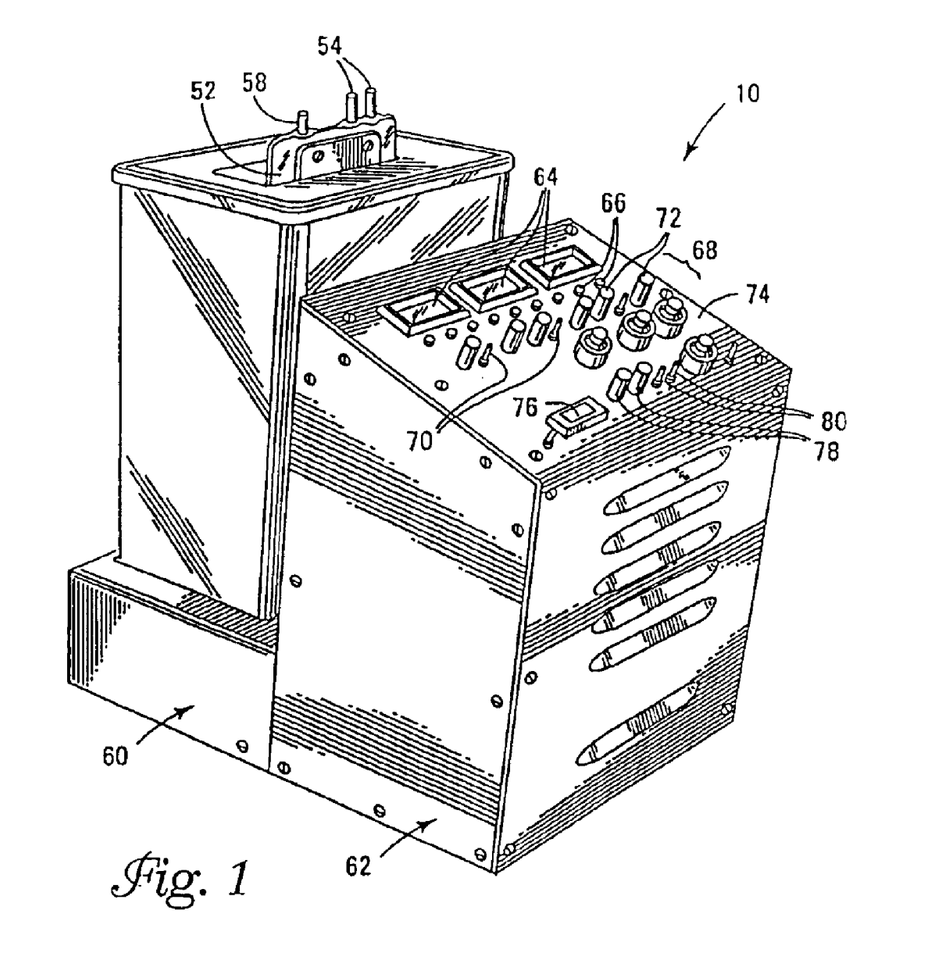
FIG. 1 is a simplified perspective view of an apparatus used to practice the invention.

FIG. 2 illustrates the series blood flow circuit 14 which included first and second cannulae for cannulating the patient at two veins, as previously discussed. A conduit 24 having a discontinuity therein was provided to interconnect, in part, the first and second cannulae. An integrated, sterile module 26, as best seen in FIG. 1, was interfaced with the discontinuity in the discontinuous conduit 24 to complete the series blood flow circuit 14. The module 26 contained all of the components which were exposed to blood in the course of a treatment. It included a conduit portion 28 which was placed in communication with segments 30 of the discontinuous conduit 24 to complete the circuit 14.

The conduit portion 28 of the disposable module 26 had different components interposed therein. Blood was pumped from the egress point 16 of cannulation at a vein to a heat exchanger 32 by means of a pump 34 of appropriate construction. FIG. 2 illustrates the centrifugal pump 34 that was used, but it will be understood that this specific type of pump is not exclusive.

FIG. 2 illustrates a heat exchanger 32 down-flow from the pump 34. The heat exchanger 32 functioned to selectively elevate the temperature of the blood to a desired level. The blood, after passing through the heat exchanger 32, passed through a perfusate filter 36. At this location, the perfusate can be purged of any impurities.

A flow probe or sensor 38 was in the series flow circuit 14 down-flow from the perfusate filter 36. The probe 38 served to sense information with regard to the measure of flow rate of the perfusate passing through the circuit 14. FIG. 2 illustrates the pressure transducer 40 that was used in the circuit 14 down-flow from the flow sensor 38. While it is important to know flow rate of the perfusate through the circuit 14, it is also important to know the pressure through the system also. Consequently, the patient being treated can be adequately protected.

FIG. 2 also illustrates the temperature sensor 42 that was used in the circuit 14. The sensor 42, of course, served to provide information with regard to the temperature of the blood flowing through the circuit 14.

FIG. 2 also shows a branch 44 of the circuit 14 which recirculated excess perfusate, not needed to be fed back into the patient, back to the pump 34 for recirculation. The recirculation branch 44 was also used during initial setup.

Also illustrated are a series of tubing clamps 46. Such clamps 46 serve, basically, as occluders which can be disposed to pinch tubing segments to preclude flow therethrough. In FIG. 2, the three such tubing clamps 46 that were used are illustrated. A first was immediately down-flow of the egress point on the patient. A second was located immediately prior to the location at which the blood reenters the patient's body. The third was positioned in the recirculation segment of the circuit 14.

FIG. 1 illustrates, as previously discussed, an integrated, sterile module 26 in which are disposed all of the components described with reference to FIG. 2 as being exposed to blood in the blood flow circuit 14. FIG. 1 also, however, illustrates the non-disposable base unit that was used including a chassis 60 which removably mounts the integrated, sterile module 26. FIG. 1 further shows that the base unit included a console or controller unit 62 for controlling operation of the hyperthermia procedure being performed. The console 62 functioned to regulate and maintain perfusate flow rate, pressure, and temperature at desired levels.

The console 62 had a series of digital display windows 64. Such windows 64 read temperature, pressure, and flow rate and displayed those parameters for both actual sensed values and inputted alarm range settings. Each display 64 was provided with a series of visual alarms (i.e., LED's 66) for signaling when, for example, a desired range within which temperature, flow rate, or pressure, is intended to be maintained, was exceeded. A series of alarm setting controls 68 were also shown as being provided. Each window 64 had corresponding upper and lower range controls and an intermediately positioned toggle switch 70. The toggle switch 70 could be toggled between positions representative of upper and lower range settings. When in an upper range setting, for example, the appropriate dial 72 could be maneuvered to adjust the upper range limit.

Finally, the control panel 74 of the console 62 had a lower row of dials, displays, etc. These components included a timer 76, rate and amplitude controls 78 for additional modes of operation (such as a pulsatile mode), and an electronic filter 80 for filtering aberrant amplitude signals regarding, for example, pressure in the circuit 14, etc.

In the structure illustrated in FIG. 1 and used to treat the patients, it is intended that the heater/cooler (not shown) for providing external fluid to the heat exchanger 32 would not comprise part of the console 62. Heat exchange was implemented in a collateral manner known in the prior art.

While not specifically shown in FIG. 1, the console 62 contained therewithin a motor 82 which interfaces, through a wall, with the perfusate pump 34. This was done by providing the motor 82 with a magnetic rotor. As the motor 82 was driven, the rotor was caused to be rotated also. A magnetic element was provided in the pump 34, and such a magnetic element interfaced, through the wall, with the magnetic rotor. Driving of the rotor, in turn, translated to operation of the pump 34 to a desired level.

Figure 3:
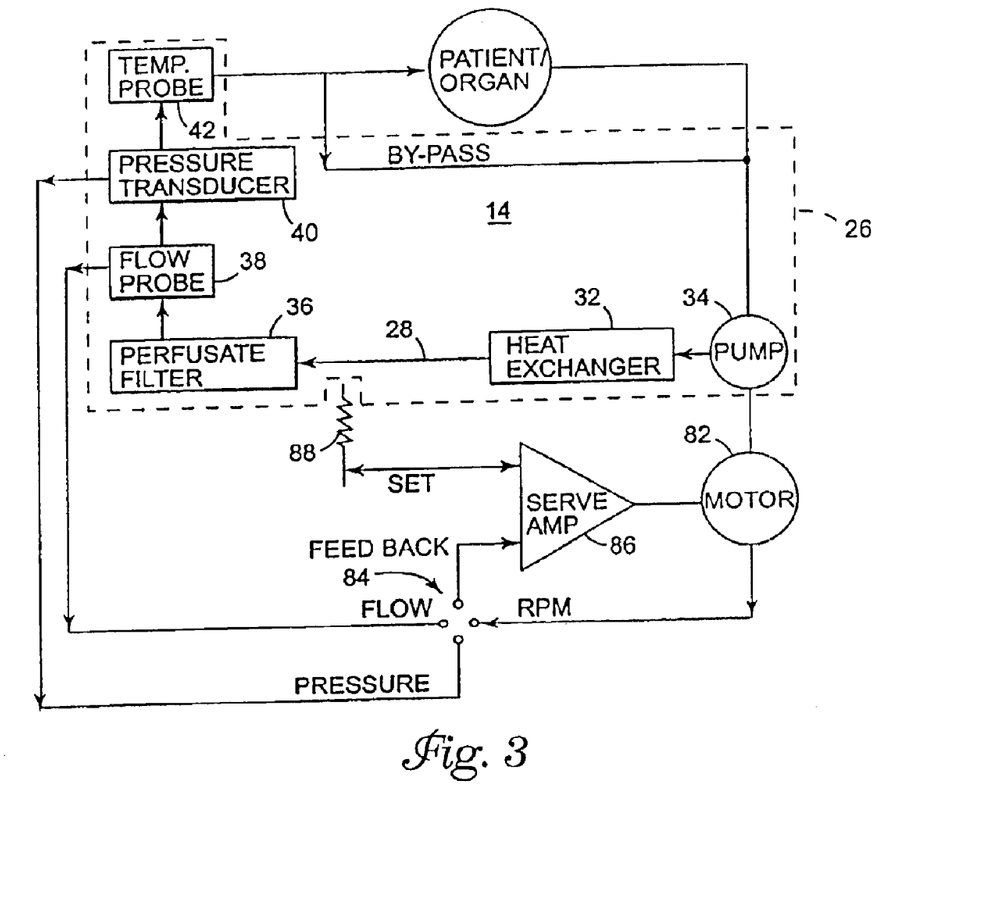
FIG. 3 is a simplified diagram of the system illustrated in FIG. 2.

FIG. 3 illustrates schematically how the pump 34, was controlled in response to pressure and flow rate levels sensed by respective sensors 38, 40. Those figures show the integrated, sterile module 26 and the components enclosed therewithin by a dotted line.

In utilizing the system for hyperthermia treatments, the patient was cannulated in the manner discussed above. Initially, the patient was out of the circuit 14, and flow bypassed the patient. This was effected by manipulation of the appropriate tube clamps 46 to effect flow through the bypass branch circuit 44.

A selector switch 84 was manually positioned so that feedback was provided from either the motor 82, the pressure transducer 40, or the flow probe 38. Input from the appropriate feedback component passed through the selector switch 84 to a servo-amplifier 86. The amplifier 86, in turn, inputted information to control the pump speed in an appropriate fashion to accomplish desired flow and pressure parameters.

FIG. 3 also illustrates a variable resistor 88 which was manipulated in initiating the setting of a particular parameter. The parameter was set and, after the system was appropriately calibrated, the patient was introduced into the flow system 14. Thereafter, continuous monitoring was performed of temperature, pressure, and flow rate. If the alarm system indicated that a parameter had gone outside the desired range, appropriate action was taken to bring the parameter back within the range.

During hyperthermia, $pCO_2$ varies directly with a change in body temperature. It is desirable to hold the bloods $CO_2$ content constant during alpha-stat regulation, thereby requiring an inverse relationship between air convection requirements and body temperature. Alpha-stat maintains constant $CO_2$ by regulating $pCO_2$. Hence, utilizing the alpha-stat technique for blood gas management is advantageous in that the pH gradient across the cellular membrane is preserved throughout the range of temperatures encountered during hyperthermia. This alpha-stat regulation of blood pH and $pCO_2$ were used in treating the patients.

By direct control of pulmonary ventilation through manipulation of respiratory rate, the $pCO_2$, the total $CO_2$, and the pH were maintained throughout the procedure according to alpha-stat parameters, ensuring that electrolyte balance was maintained throughout. No electrolyte replacement was required in any patient during the procedure, nor was there ever a need to administer sodium bicarbonate for metabolic acidosis.

The blood flow circuit comprised a Blood Gas Analyzer (BGA). Within the BGA is an analyzer which analyzes the blood gases, including the blood pH and $pCO_2$ through infrared or chemical analysis. A pulse oximeter attached to the patient through suitable means, measured the $pO_2$ of a patient's blood. The microprocessor then analyzed the data associated with the blood's pH, $pCO_2$, $pO_2$ and calculated the base excess of the blood normalized at 37° C. The microprocessor was programmed to then automatically adjust the respiratory rate of the patient and either the amount of $NaHCO_3$ or acidotic crystalloid solution (which affects the $HCO_3^-$ ion concentration) being introduced into the patient's blood. This was accomplished by adjusting the respiratory rate of the patient through ventilation or medications.

The respiratory management of the blood at constant $CO_2$ content, while the temperature was changed, maintained a constant alpha thereby stabilizing the biochemical reactions fundamental to the metabolic welfare of components of the patient's blood. The sodium bicarbonate buffering system was based upon the following equation:

$$H^+ + HCO_3^- \sim H_2CO_3 \sim H_2O + CO_2$$

Acidosis (↓pH) occurs when there is an increase of H+ (metabolic) and/or $CO_2$ (respiratory). Respiratory acidosis was treated with changes in depth of ventilation or ventilatory rate. Metabolic acidosis was treated with the administration of sodium bicarbonate ($NaHCO_3$). "Bicarb" dissociates into Na+ and $HCO_3^-$ which combines with H+ to form $CO_2$ and $H_2O$.

The blood gases, pH, $PO_2$, $pCO_2$, and $HCO_3^-$ concentration were obtained by direct measurement. Base excess (BE) is a derived parameter based upon the relationship between the measured $pCO_2$, and $HCO_3^-$ concentration, and is calculated relative to the normal $HCO_3^-$ centration values: 24 mEq/L in arterial blood and 26 mEq/L in venous blood.

Optional Equipment that was not Used

A thermal sensor and bladder catheter that were not used to treat the patients are described below.

Thermal Sensor

An improved temperature monitoring device suited to extracorporeal whole body hyperthermia can be used.

The sensor described is connected to the blood flow circuit near the patient. The temperature sensor has a very small mass and is place on a strut. The strut places the thermal sensor in the laminar blood flow of a duct or fitting. In this fashion, a fast reacting thermal assessment may be made of blood temperature as blood enters or leaves the body.

Figure 4:
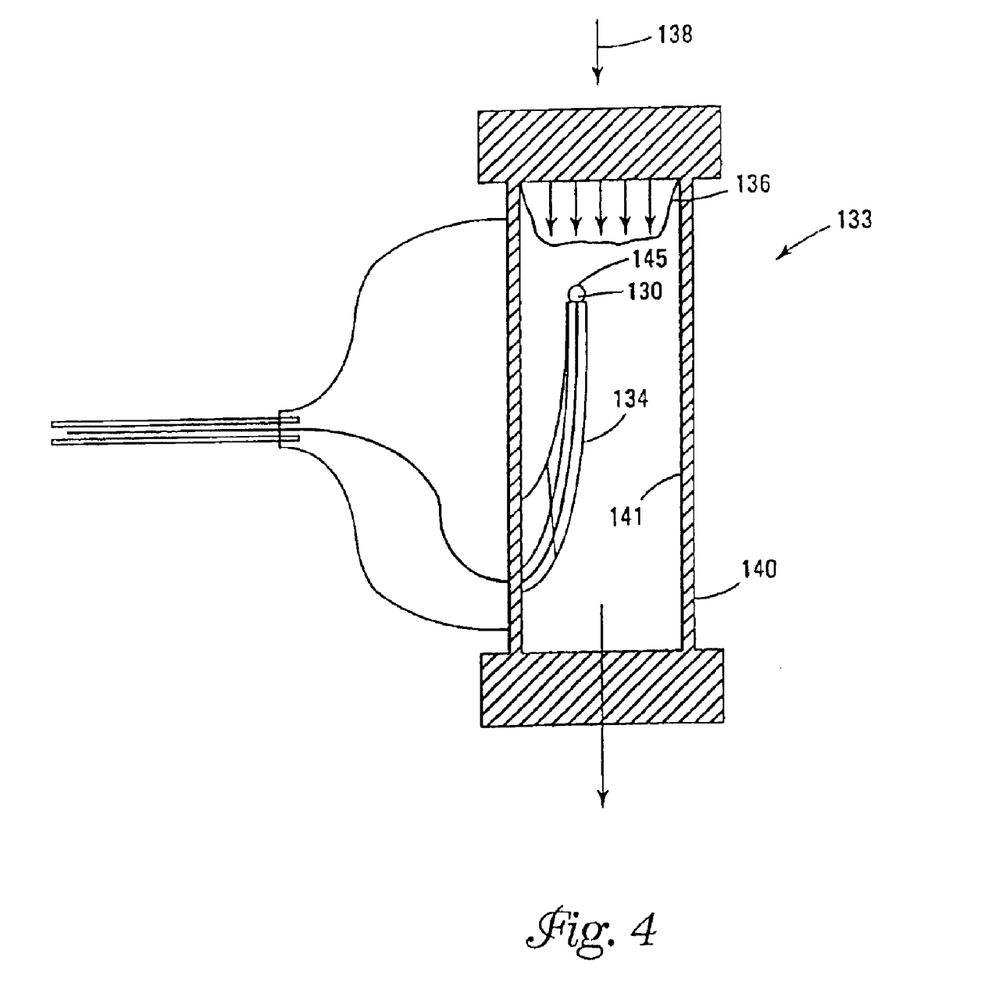
FIG. 4 is a cross-section of a temperature sensor.

FIG. 4 illustrates a temperature probe 133 for supporting the temperature sensor 130 in the flow of blood moving through a hyperthermia system. As shown in FIG. 4, the probe 133 includes a tube or flow-directing passage 140 having a wall defining an interior lumen 141. Although a cylindrical shape is shown and is preferred to minimize wetted surface area, other cross-sectional shapes are operable. As shown in FIG. 4, the cross-sectional area of the lumen 141 remains constant in the direction of flow indicated by arrow 138. It should be appreciated that the lumen 141 may decrease in cross-sectional area in the direction of flow to maintain laminar flow past the strut 134.

A temperature sensor 130 is attached to the strut 134. Preferably, the strut 134 is shaped and positioned such that the sensor 30 supported thereon is placed in a region of laminar flow and preferably near a location of maximum flow velocity. A region of laminar flow is illustrated in the velocity profile 136. More specifically, the strut 134 is shaped and positioned such that at least a portion of strut 134 lies upstream of the site at which the strut 134 attaches to or passes through the tube 140. The preferred strut 134 has a generally arcuate shape along its length. As shown in the embodiment illustrated in FIG. 4, the strut 134 has a terminating tip 145 that is positioned near the axial center of the tube 140 where the blood flow achieves maximum velocity. In this fashion the sensor 130 is located in the maximum flow zone in the device and can sense subtle changes in blood temperature. By positioning the sensor "in-line", or in the flow of blood as it passes through the system, advantages are achieved. For example, the laminar flow prevents disruption of the blood and temperature change due to mixing. This factor combined with the fast response small thermal mass sensor 130 improves control of body temperature.

The preferred form of the probe 133 includes fittings which may be barbed. These allow the device to be positioned close to the patient. It is believed that monitoring in close proximity to the patient is desirable to minimize heat loss to the environment.

More than one sensor can be used in a hyperthermic system. The use of a second sensor increases the ability of the system to accurately monitor and control temperature.

The sensors 130 and 132 may be of any temperature-sensing type, such as thermistors, thermocouples, and the like.

Bladder Catheter

An improved catheter can be used in the whole body hyperthermia system. In use, the catheter is suspended in the bladder of the patient. A cuff on the catheter inflates after the catheter is inserted in the bladder to assist in positioning and securing the catheter. The catheter has a temperature sensor proximal of the inflatable cuff to measure body temperature at the urinary sphincter muscle. The sensor is located relative to the cuff a distance know to generally correspond to the typical distance between the bladder and the sphincter muscle in humans. This distance is known to be approximately the same amongst humans regardless of size.

In an alternative catheter, a second temperature sensor is placed distal of the inflatable cuff and thus monitors the temperature of the urine pool in the bladder. Each of the measurements from the first and second temperature sensors has a different time constant depending on the volume of urine in the bladder, and the level of perfusion in the sphincter. Data from these two sensors, the differences between the readings, and the time-dependent variation of these two sensors can contribute to the overall efficacy of the device.

An exemplary version of the bladder catheter is shown in the figures in which like reference numerals refer to equivalent structure throughout.

Figure 5:
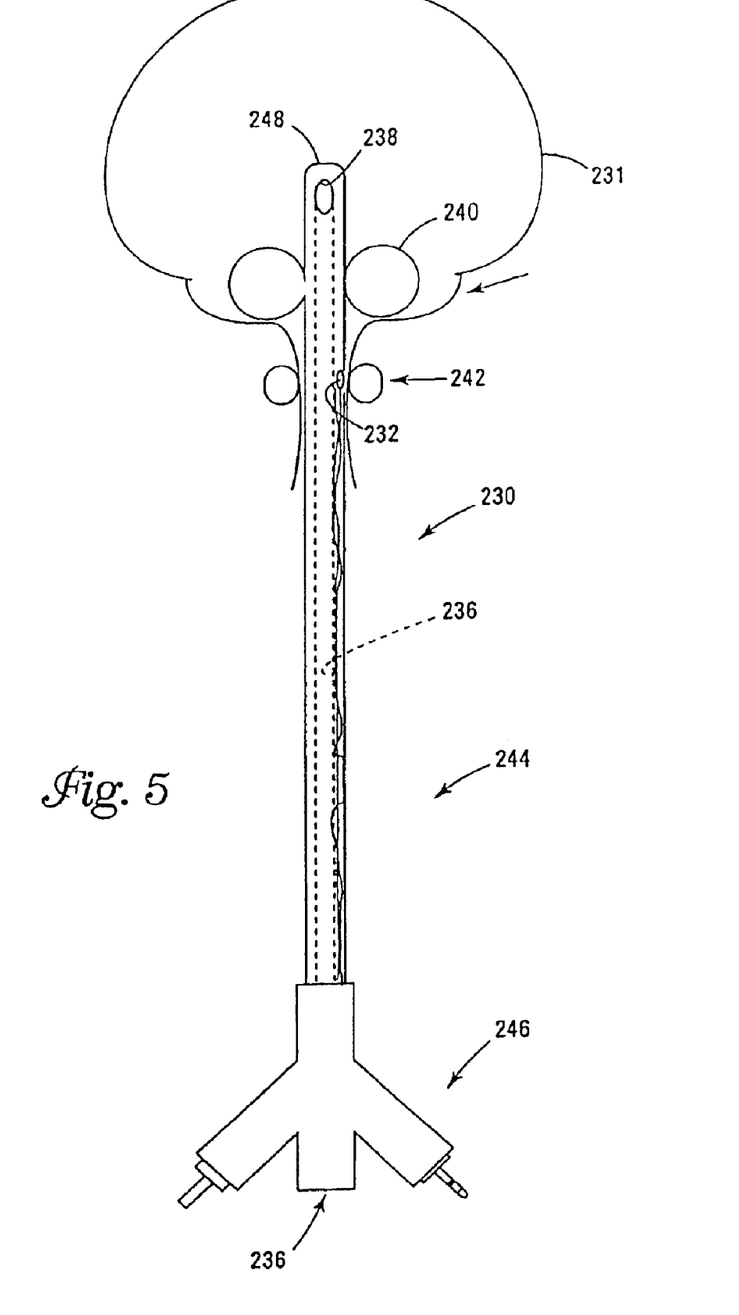
FIG. 5 is a cross-section of a temperature catheter having a temperature sensor positioned at the urinary sphincter muscle with the aid of an inflatable cuff that engages the bladder wall.

FIG. 5 shows a bladder temperature probe 230 having an elongate body 244 and terminating in a proximal end 246 and further having a distal tip 248 and a first temperature sensor 232, which may be of any conventional type, including thermistors, thermocouples or other solid state temperature sensors. A drainage lumen 236 communicates with a distal opining 238 to allow fluid to be withdrawn from the bladder 231 or to allow fluid, such as saline, to be infused into the bladder. An inflatable distal cuff 240 positions the catheter and prevents its removal from the bladder while the cuff is inflated. The sensor 232 and the inflatable cuff are spaced and oriented such that when the inflatable cuff 240 holds the probe 230 in position in the patient's bladder 231, the sensor 232 is located proximal of the urinary sphincter muscle 242. Temperature information gathered at this site from the surrounding tissue is likely to be reliable and somewhat less subject to rapid fluctuation than a temperature reading taken from other locations, such as the urine pool.

Figure 6:
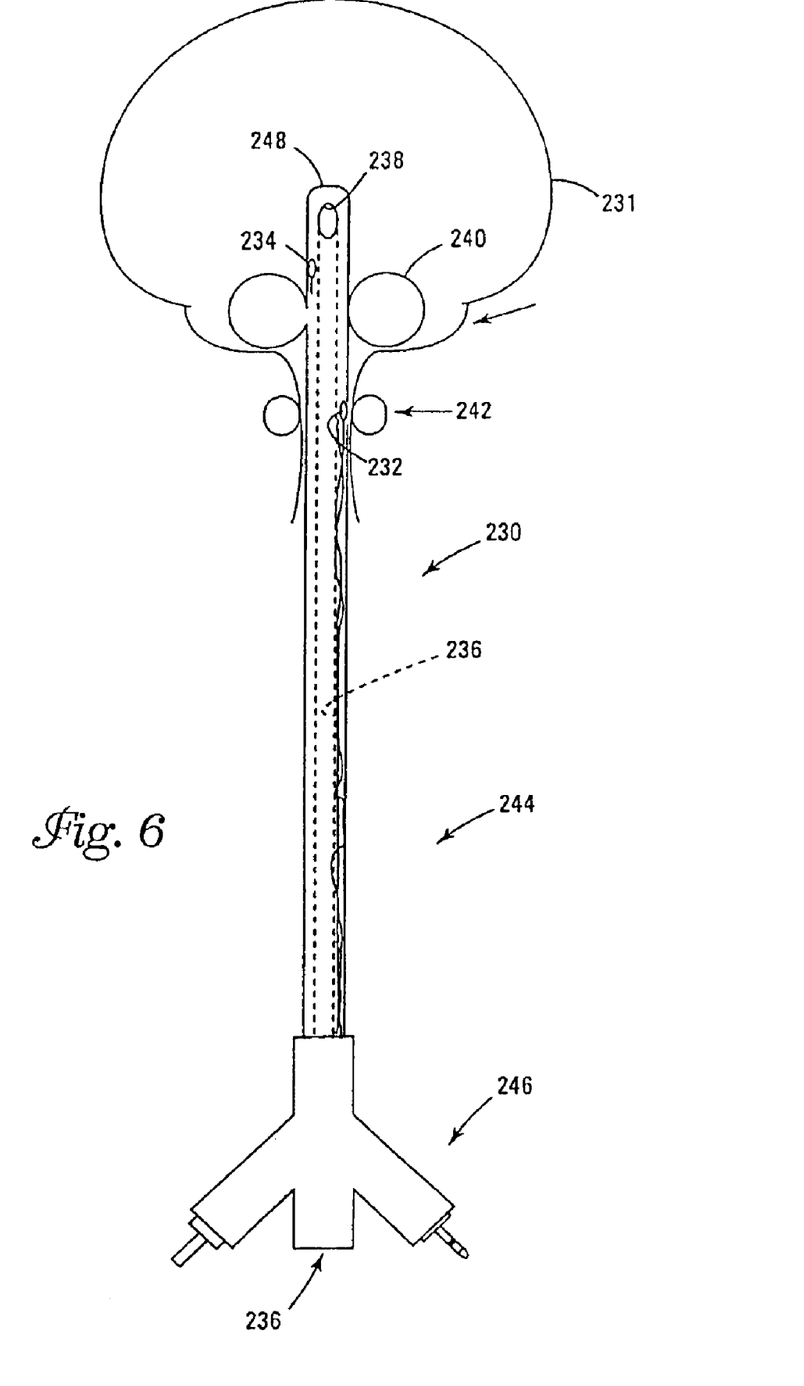
FIG. 6 is a cross-section of temperature catheter having two temperature sensors, one of which is positioned at the urinary sphincter muscle with the aid of an inflatable cuff the engages the bladder wall and the second of which is positioned in the urine pool.

In an alternate catheter, illustrated in FIG. 6, the catheter carries a second temperature sensor 234. In practice, the cuff positions the second temperature sensor 234 in the bladder urine or fluid pool while the first sensor 232 is located adjacent the musculature near the sphincter 242. It is expected that the two sensors will vary in measured temperature as the effective time constants for the two locations differ. These two temperatures and relative rates of their variation contribute to the efficacy of body temperature control.

Computerized controls can be added to all of the equipment described above.

The above description is provided for the purpose of describing embodiments of the invention and is not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents.

What is claimed is:

1. A method for treating a patient infected with hepatitis C virus (HCV) comprising raising the core temperature of the patient and then returning the core temperature of the patient to normal at least one time, wherein the core temperature is raised to a temperature range and a duration sufficient to reduce the patient's viral load of HCV by 30 percent or more three months after the core temperature has been raised and returned to normal said at least one time, wherein the patient's viral load of HCV is determined at least once after the core temperature has been raised and returned to normal said at least one time, and wherein the patient is treated with a pharmaceutical indicated for hepatitis C that is selected from ribavirin, lamivudine, interferon alfacon-1, interferon alfa-2a, interferon alfa-2b, interferon-alfa-n1, thymosin alpha-1, interleukin-2, interferon alpha-n3, ketoprofen, interferon beta-1a, interferon gamma-1b, interleukin-12, or combinations thereof.

2. A method according to claim 1, wherein the pharmaceutical is ribavirin.

3. A method according to claim 1, wherein the pharmaceutical is lamivudine.

4. A method according to claim 1, wherein the pharmaceutical is interferon alfacon-1.

5. A method according to claim 1, wherein the pharmaceutical is interferon alfa-2a.

6. A method according to claim 1, wherein the pharmaceutical is interferon alfa-2b.

7. A method according to claim 1, wherein the pharmaceutical is interferon-alfa-n1.

8. A method according to claim 1, wherein the pharmaceutical is thymosin alpha-1.

9. A method according to claim 1, wherein the pharmaceutical is interleukin-2.

10. A method according to claim 1, wherein the pharmaceutical is interferon alpha-n3.

11. A method according to claim 1, wherein the pharmaceutical is ketoprofen.

12. A method according to claim 1, wherein the pharmaceutical is interferon beta-1a.

13. A method according to claim 1, wherein the pharmaceutical is interferon gamma-1b.

14. A method according to claim 1, wherein the pharmaceutical is interleukin-12.

15. A method for treating a patient infected with hepatitis C virus (HCV) comprising raising the core temperature of the patient and then returning the core temperature of the patient to normal at least one time, wherein the core temperature is raised to a temperature range and a duration sufficient to reduce the patient's viral load of HCV by 30 percent or more one month after the core temperature has been raised and returned to normal said at least one time, wherein the patient's viral load of HCV is determined at least once after the core temperature has been raised and returned to normal said at least one time, and wherein the patient is treated with a pharmaceutical indicated for hepatitis C that is selected from ribavirin, lamivudine, interferon alfacon-1, interferon alfa-2a, interferon alfa-2b, interferon-alfa-n1, thymosin alpha-1, interleukin-2, interferon alpha-n3, ketoprofen, interferon beta-1a, interferon gamma-1b, interleukin-12, or combinations thereof.

16. A method according to claim 15, wherein the pharmaceutical is ribavirin.

17. A method according to claim 15, wherein the pharmaceutical is lamivudine.

18. A method according to claim 15, wherein the pharmaceutical is interferon alfacon-1.

19. A method according to claim 15, wherein the pharmaceutical is interferon alfa-2a.

20. A method according to claim 15, wherein the pharmaceutical is interferon alfa-2b.

21. A method according to claim 15, wherein the pharmaceutical is interferon-alfa-n1.

22. A method according to claim 15, wherein the pharmaceutical is thymosin alpha-1.

23. A method according to claim 15, wherein the pharmaceutical is interleukin-2.

24. A method according to claim 15, wherein the pharmaceutical is interferon alpha-n3.

25. A method according to claim 15, wherein the pharmaceutical is ketoprofen.

26. A method according to claim 15, wherein the pharmaceutical is interferon beta-1a.

27. A method according to claim 15, wherein the pharmaceutical is interferon gamma-1b.

28. A method according to claim 15, wherein the pharmaceutical is interleukin-12.

29. A method for treating a patient infected with hepatitis C virus (HCV) comprising raising the temperature of the patient's liver and then returning the temperature of the patient's liver to normal at least one time, wherein the temperature of the patient's liver is raised to a temperature range and a duration sufficient to reduce the patients viral load of HCV by 30 percent or more three months after the temperature of the patient's liver has been raised and returned to normal said at least one time, wherein the patient's viral load of HCV is determined at least once after the temperature of the patient's liver has been raised and returned to normal said at least one time, and wherein the patient is treated with a pharmaceutical indicated for hepatitis C that is selected from ribavirin, lamivudine, interferon alfacon-l, interferon alfa-2a, interferon alfa-2b, interferon-alfa-n1, thymosin, interleukin-2, interferon alpha-n3, ketoprofen, interferon beta-1a, interferon gamma-1b, interleukin-12, or combinations thereof.

30. A method according to claim 29, wherein the pharmaceutical is ribavirin.

31. A method according to claim 29, wherein the pharmaceutical is lamivudine.

32. A method according to claim 29, wherein the pharmaceutical is interferon alfacon-1.

33. A method according to claim 29, wherein the pharmaceutical is interferon alfa-2a.

34. A method according to claim 29, wherein the pharmaceutical is interferon alfa-2b.

35. A method according to claim 29, wherein the pharmaceutical is interferon-alfa-n1.

36. A method according to claim 29, wherein the pharmaceutical is thymosin alpha-1.

37. A method according to claim 29, wherein the pharmaceutical is interleukin-2.

38. A method according to claim 29, wherein the pharmaceutical is interferon alpha-n3.

39. A method according to claim 29, wherein the pharmaceutical is ketoprofen.

40. A method according to claim 29, wherein the pharmaceutical is interferon beta-1a.

41. A method according to clam 29, wherein the pharmaceutical is interferon gamma-1b.

42. A method according to claim 29, wherein the pharmaceutical is interleukin-12.

43. A method for treating a patient infected with hepatitis C virus (HCV) comprising raising the temperature of the patient's liver and then returning the temperature of the patient's liver to normal at least one time, wherein the temperature of the patient's liver is raised to a temperature range and a duration sufficient to reduce the patient's viral load of HCV by 30 percent or more one month after the temperature of the patient's liver has been raised and returned to normal said at least one time, wherein the patient's viral load of HCV is determined at least once after the temperature of the patient's liver has been raised and returned to normal said at least one time, and wherein the patient is treated with a pharmaceutical indicated for hepatitis C that is selected from ribavirin, lamivudine, interferon alfacon-1, interferon alfa-2a, interferon alfa-2b, interferon-alfa-n1, thymosin alpha-1, interleukin-2, interferon alpha-n3, ketoprofen, interferon beta-1a, interferon gamma-1b, interleukin-12, or combinations thereof.

44. A method according to claim 43, wherein the pharmaceutical is ribavirin.

45. A method according to claim 43, wherein the pharmaceutical is lamivudine.

46. A method according to claim 43, wherein the pharmaceutical is interferon alfacon-1.

47. A method according to claim 43, wherein the, pharmaceutical is interferon alfa-2a.

48. A method according to claim 43, wherein the pharmaceutical is interferon alfa-2b.

49. A method according to claim 43, wherein the pharmaceutical is interferon-alfa-n1.

50. A method according to claim 43, wherein the pharmaceutical is thymosin alpha-1.

51. A method according to claim 43, wherein the pharmaceutical is interleukin-2.

52. A method according to claim 43, wherein the pharmaceutical is interferon alpha-n3.

53. A method according to claim 43, wherein the pharmaceutical is ketoprofen.

54. A method according to claim 43, wherein the pharmaceutical is interferon beta-1a.

55. A method according to claim 43, wherein the pharmaceutical is interferon gamma-1b.

56. A method according to claim 43, wherein the pharmaceutical is interleukin-12.

* * * * *